(12) United States Patent
Ghosh et al.

(10) Patent No.: US 9,756,860 B2
(45) Date of Patent: Sep. 12, 2017

(54) ANTIMICROBIAL COMPOSITION OF ORTHO PHENYLPHENOL AND SILVER

(71) Applicant: Rohm and Haas Company, Philadelphia, PA (US)

(72) Inventors: Tirthankar Ghosh, Oreland, PA (US); Kiran Pareek, Bensalem, PA (US); Thomas D. Rogerson, Chalfont, PA (US)

(73) Assignee: ROHM AND HAAS COMPANY, Philadelphia, PA (US)

( * ) Notice: Subject to any disclaimer, the term of this patent is extended or adjusted under 35 U.S.C. 154(b) by 91 days.

(21) Appl. No.: 14/362,128

(22) PCT Filed: Nov. 27, 2012

(86) PCT No.: PCT/US2012/066648
§ 371 (c)(1),
(2) Date: Jun. 1, 2014

(87) PCT Pub. No.: WO2013/082025
PCT Pub. Date: Jun. 6, 2013

(65) Prior Publication Data
US 2014/0328942 A1    Nov. 6, 2014

Related U.S. Application Data

(60) Provisional application No. 61/565,654, filed on Dec. 1, 2011.

(51) Int. Cl.
*A01N 59/16* (2006.01)
*A01N 31/08* (2006.01)

(52) U.S. Cl.
CPC ............ *A01N 59/16* (2013.01); *A01N 31/08* (2013.01)

(58) Field of Classification Search
CPC ..... A01N 59/16; A01N 2300/00; A01N 31/08
USPC ....................................................... 424/618
See application file for complete search history.

(56) References Cited

U.S. PATENT DOCUMENTS 7,390,774 B2    6/2008    Ghosh et al.
7,927,379 B2    4/2011    Cottrell et al.

FOREIGN PATENT DOCUMENTS

WO    WO 0057933 A1 * 10/2000

* cited by examiner

*Primary Examiner* — Robert Cabral
(74) *Attorney, Agent, or Firm* — Tifani M. Edwards

(57) ABSTRACT

Provided are antimicrobial compositions comprising: ortho phenylphenol and silver. The compositions are useful for controlling microorganisms in aqueous or water-containing systems.

4 Claims, No Drawings

ANTIMICROBIAL COMPOSITION OF ORTHO PHENYLPHENOL AND SILVER

BACKGROUND

The invention relates to an antimicrobial composition and method of use for the control of microorganisms. The composition comprises ortho phenylphenol and silver.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature or high pH. Combinations of different antimicrobial compounds are sometimes used to provide overall control of microorganisms or to provide the same level of microbial control at lower use rates in a particular end use environment. There is a need, therefore, for new combinations of antimicrobial compounds having enhanced activity to provide effective control of microorganisms. The problem addressed by this invention is to provide such combinations of antimicrobial compounds.

STATEMENT OF INVENTION

The invention provides an antimicrobial composition comprising ortho phenylphenol and silver.

The invention also provides a method for controlling microorganisms in aqueous or water-containing systems. The method comprises treating the system with an effective amount of an antimicrobial composition as described herein.

DETAILED DESCRIPTION

As noted above, the invention provides an antimicrobial compositions and methods of using the composition in the control of microorganisms. The composition comprises ortho phenylphenol and silver. It has surprisingly been discovered that combinations of ortho phenylphenol and silver as described herein, at certain weight ratios, are synergistic when used for microorganism control. That is, the combined materials result in improved antimicrobial properties than would otherwise be expected based on their individual performance at the particular use-concentration. The observed synergy permits reduced amounts of the materials to be used to achieve acceptable antimicrobial properties.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism growth.

The composition of the invention comprises: ortho phenylphenol and silver. Ortho phenylphenol may be obtained from various commercial sources or it may be prepared by those skilled in the art using known techniques.

The silver may be in any form that is capable of reacting with a cellular component of a microorganism, including an ionic or non-ionic form. The silver is preferably obtained from an inorganic or organic source or by electrolytic generation of silver ions. Examples include, but are not limited to one or more of the following: silver acetate, silver acetylacetonate, silver arsenate, silver benzoate, silver bromate, silver bromide, silver carbonate, silver chlorate, silver chloride, silver chromate, silver citrate hydrate, silver cyanate, silver cyclohexanebutyrate, silver fluoride, silver heptafluorobutyrate, silver hexafluoroantimonate, silver hexafluoroarsenate, silver hexafluorophosphate, silver hydrogen fluoride, silver iodate, silver iodide, silver lactate, silver metavanadate, silver methanesulfonate, silver methenamine, silver molybdate, silver nitrate, silver nitrite, silver oxide, silver pentafluoropropionate, silver perchlorate hydrate, silver perchlorate monohydrate, silver perchlorate, silver phosphate, silver phthalocyanine, silver picolinate, silver protein, silver proteinate, silver p-toluenesulfonate, silver selenide, silver sulfadiazine, silver sulfate, silver sulfide, silver sulfite, silver telluride, silver tetrafluoroborate, silver thiocyanate, silver trifluoroacetate, silver trifluoromethanesulfonate, or silver tungstate. A preferred source is silver nitrate. The silver can also be obtained from a formulation designed to control the release of silver. Examples of controlled release formulations of silver include those based on organic polymers, zeolites, glass, calcium phosphate, titanium dioxide and zinc oxide. These formulations can employ the various inorganic or organic silver forms mentioned above. Examples of controlled release formulations of silver also include those described in U.S. Pat. Nos. 7,390,774, 7,927,379, each of which is incorporated herein by reference.

In some embodiments, the weight ratio of ortho phenylphenol to silver in the composition of the invention is between and 1:0.5 and 1:0.0004, alternatively between 1:0.5 and 1:0.005, alternatively between 1:0.2 and 1:0.0004, or alternatively between 1:035 and 1:004.

In some embodiments, the microorganism being controlled by the composition of the invention is a gram positive bacteria, such as *Staphylococcus aureus*. In some embodiments, the microorganism is yeast, *Candida albicans*. In some embodiments the microorganism is mold, such as *Aspergillus niger*. In some embodiments, the microorganism is gram negative bacteria, such as *Pseudomonas aeruginosa*.

The compositions of the invention may contain additional components including, but not limited to, surfactants, stabilizers, demulsifier, polymers, and/or additional biocides.

The compositions of the invention are useful for controlling microorganisms a variety of media, such as aqueous or water-containing systems. In some embodiments, the aqueous or water containing system comprises at least 40 weight percent, alternatively at least 60 weight percent, or alternatively at least 80 weight percent of water. Non-limiting examples of aqueous or water containing systems with which the inventive compositions may be used to control microorganisms in oil and natural gas applications, cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care products such as shampoos and lotions, and household, industrial and institutional products such as cleaners, polishes and detergents, membrane and filtration systems, textiles, leather and leather production system, or a system used therewith.

A person of ordinary skill in the art can readily determine, without undue experimentation, the concentration of the composition that should be used in any particular application. By way of illustration, a suitable actives concentration (total for both the ortho phenylphenol and silver) is typically between 1 and 2500 ppm, alternatively between 5 and 1000 ppm, alternatively between 10 and 500 ppm, or alternatively between 50 and 300 ppm, based on the total weight of the aqueous or water-containing system including the biocides.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

The following examples are illustrative of the invention but are not intended to limit its scope. Unless otherwise indicated, ratios, percentages, parts, and the like used herein are by weight.

EXAMPLES

Ortho phenylphenol and silver are evaluated for synergy by determining the synergy index (S.I.) of the combination. Synergy index is calculated based on minimum inhibitory concentrations (MIC) of two antimicrobial compounds (A and B) alone and in combinations. The tests organisms are Gram negative bacteria (*Pseudomonas aeruginosa*), Gram positive bacteria (*Staphylococcus aureus*), yeast (*Candida albicans*) and mold (*Aspergillus niger*). Contact time for the bacteria is 24 and 48 hours, yeast is 48 and 72 hrs, and 3 and 7 days for mold. The test is carried out in 96 well microtiter plates. More details on the tests are shown in Tables 1-3.

TABLE 1

Preservatives Used

| Abbreviations | Compound | Supplier | AI %[1] | Solvent |
|---|---|---|---|---|
| Slow release delivery system 1[3] | Silver | The Dow Chemical Co. | 3 | MQ[2] H$_2$O |
| Slow release delivery system 2[3] | Silver | The Dow Chemical Co. | 2.2 | MQ H$_2$O |
| AgNO3 | Silver | — | 100% | MQ H$_2$O |
| OPP | Ortho-phenylphenol | The Dow Chemical Co. | 99.5% | Ethanol |

[1]AI = active ingredient;
[2]MQ = Milli Q water (brand of water purification);
[3]liquid formulations of silver with polymers

TABLE 2

Inoculums Used
Inoculum Size of organisms (CFU/ml)

| Staphylococcus. aureus ATCC# 6538 | Pseudomonas aeruginosa ATCC # 15442 | Aspergillus niger ATCC# 16404 | Candida albicans ATCC#10203 |
|---|---|---|---|
| 5.7 × 10$^5$ | 5.7 × 10$^6$ | 1.5 × 10$^5$ | 1.5 × 10$^5$ |

TABLE 3

Media Used
Media Used for testing

| Staphylococcus. aureus ATCC# 6538 | Pseudomonas aeruginosa ATCC # 15442 | Aspergillus niger ATCC# 16404 | Candida albicans ATCC#10203 |
|---|---|---|---|
| 10% Tryptic soy broth | M9GY (minimal salt media supplemented with 0.2% glucose and 0.1% yeast extract) | Potato dextrose broth | Potato dextrose broth |

The test results for demonstration of synergy of the MIC combinations are shown below in Tables 4-6. Each Table shows the combinations of two components results against the microorganisms tested with incubation times; the end-point activity in ppm measured by the MIC for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index ("SI")}$$

Wherein:
CA=concentration of compound A in ppm, acting alone, which produced an end point (MIC of Compound A).
Ca=concentration of compound A in ppm, in the mixture, which produced an end point.
CB=concentration of compound B in ppm, acting alone, which produced an end point (MIC of Compound B).
Cb=concentration of compound B in ppm, in the mixture, which produced an end point.

When the sum of Ca/CA and Cb/CB is greater than one, antagonism is indicated. When the sum is equal to one, additivity is indicated, and when less than one, synergism is demonstrated.

TABLE 4

| Test Organisms | Contact Time | Ca | Cb | S.I. | Ca:Cb |
|---|---|---|---|---|---|
| A. niger ATCC #16404 | 3rd day | 75 | — | — | — |
| | | — | 3 | — | — |
| | | 35 | 0.2 | 0.53 | 1:0.0057 |
| | | 35 | 0.4 | 0.60 | 1:0.0114 |
| | | 35 | 0.6 | 0.67 | 1:0.0171 |
| | | 35 | 1 | 0.80 | 1:0.0286 |
| | | 35 | 2 | 1.13 | 1:0.0571 |
| | | 17 | 2 | 0.89 | 1:0.1176 |
| | | 17 | 3 | 1.23 | 1:0.1765 |
| | 7th day | 75 | — | — | — |
| | | — | 10 | — | — |
| | | 35 | 2 | 0.67 | 1:0.0571 |
| | | 35 | 3 | 0.77 | 1:0.0857 |
| | | 35 | 4 | 0.87 | 1:0.1143 |
| | | 35 | 6 | 1.07 | 1:0.1714 |
| | | 17 | 3 | 0.53 | 1:0.1765 |
| | | 17 | 6 | 0.83 | 1:0.3529 |
| | | 17 | 8 | 1.03 | 1:0.4706 |
| C. albicans ATCC#10203 | 48 hrs | 150 | — | — | — |
| | | — | 10 | — | — |
| | | 75 | 2 | 0.70 | 1:0.0267 |
| | | 75 | 3 | 0.80 | 1:0.0400 |
| | | 75 | 4 | 0.90 | 1:0.0533 |
| | | 75 | 5 | 1.00 | 1:0.0667 |
| | | 35 | 5 | 0.73 | 1:0.1429 |
| | | 35 | 6 | 0.83 | 1:0.1714 |
| | | 35 | 7 | 0.93 | 1:0.2000 |
| | | 35 | 8 | 1.03 | 1:0.2286 |
| | | 17 | 8 | 0.91 | 1:0.4706 |
| | | 17 | 9 | 1.01 | 1:0.5294 |

TABLE 4-continued

| Test Organisms | Contact Time | Ca | Cb | S.I. | Ca:Cb |
|---|---|---|---|---|---|
| | 72 hrs | 150 | — | — | — |
| | | — | 10 | — | — |
| | | 75 | 3 | 0.80 | 1:0.0400 |
| | | 75 | 4 | 0.90 | 1:0.0533 |
| | | 75 | 5 | 1.00 | 1:0.0667 |
| | | 75 | 5 | 1.00 | 1:0.0667 |
| | | 35 | 5 | 0.73 | 1:0.1429 |
| | | 35 | 6 | 0.83 | 1:0.1714 |
| | | 35 | 7 | 0.93 | 1:0.2000 |
| | | 35 | 8 | 1.03 | 1:0.2286 |
| | | 17 | 8 | 0.91 | 1:0.4706 |
| | | 17 | 9 | 1.01 | 1:0.5294 |
| Ps. aeruginosa ATCC#15442 | 24 hrs | 500 | — | — | — |
| | | — | 0.4 | — | — |
| | | 250 | 0.3 | 1.25 | 1:0.0012 |
| | | 125 | 0.3 | 1.00 | 1:0.0024 |
| | | 125 | 0.4 | 1.25 | 1:0.0032 |
| | 48 hrs | 500 | — | — | — |
| | | — | 1 | — | — |
| | | 250 | 0.3 | 0.80 | 1:0.0012 |
| | | 250 | 0.4 | 0.90 | 1:0.0016 |
| | | 250 | 0.6 | 1.1 | 1:0.0024 |
| | | 125 | 0.4 | 0.65 | 1:0.0032 |
| | | 125 | 0.6 | 0.85 | 1:0.0048 |
| | | 125 | 0.8 | 1.05 | 1:0.0064 |
| S. aureus ATCC#6538 | 24 hrs | 200 | — | — | — |
| | | — | 6 | — | — |
| | | 100 | 5 | 1.33 | 1:0.0500 |
| | | 50 | 6 | 1.25 | 1:0.1200 |
| | | 25 | 6 | 1.13 | 1:0.2400 |
| | 48 hrs | 200 | — | — | — |
| | | — | 8 | — | — |
| | | 100 | 6 | 1.25 | 1:0.0600 |
| | | 50 | 8 | 1.25 | 1:0.1600 |
| | | 25 | 8 | 1.13 | 1:0.3200 |

Ca: component in ppm active concentration of OPP(ortho-phenylphenol)
Cb: component in ppm active concentration of AgNO3 (Silver Nitrate)

The data in Table 4 demonstrate that there is an unexpected synergistic interaction between OPP and silver at ratios of 1:0.0012 to 1:4706.

TABLE 5

| Test Organisms | Contact Time | Ca | Cb | S.I. | Ca:Cb |
|---|---|---|---|---|---|
| A. niger ATCC #16404 | 3rd day | 75 | — | — | — |
| | | — | 3 | — | — |
| | | 35 | 0.2 | 0.53 | 1:0.0057 |
| | | 35 | 0.4 | 0.60 | 1:0.0114 |
| | | 35 | 0.6 | 0.67 | 1:0.0171 |
| | | 35 | 1 | 0.80 | 1:0.0286 |
| | | 35 | 2 | 1.13 | 1:0.0571 |
| | | 17 | 2 | 0.89 | 1:0.1176 |
| | | 17 | 3 | 1.23 | 1:0.1765 |
| | 7th day | 75 | — | — | — |
| | | — | 6 | — | — |
| | | 35 | 2 | 0.8 | 1:0.0571 |
| | | 35 | 3 | 0.97 | 1:0.0857 |
| | | 35 | 4 | 1.13 | 1:0.1143 |
| | | 17 | 3 | 0.73 | 1:0.1765 |
| | | 17 | 4 | 0.89 | 1:0.2353 |
| | | 17 | 5 | 1.06 | 1:0.2941 |
| C. albicans ATCC#10203 | 48 hrs | 150 | — | — | — |
| | | — | 5 | — | — |
| | | 75 | 3 | 1.1 | 1:0.0400 |
| | | 35 | 4 | 1.03 | 1:0.1143 |
| | | 17 | 4 | 0.91 | 1:0.2353 |
| | | 17 | 5 | 1.11 | 1:0.2941 |
| | 72 hrs | 150 | — | — | — |
| | | — | 5 | — | — |
| | | 75 | 3 | 1.1 | 1:0.0400 |
| | | 35 | 4 | 1.03 | 1:0.1143 |
| | | 17 | 5 | 1.11 | 1:0.2941 |
| Ps. aeruginosa ATCC#15442 | 24 hrs | 500 | — | — | — |
| | | — | 0.4 | — | — |
| | | 250 | 0.1 | 0.75 | 1:0.0004 |
| | | 250 | 0.2 | 1.00 | 1:0.0008 |
| | | 250 | 0.3 | 1.25 | 1:0.0012 |
| | 48 hrs | 500 | — | — | — |
| | | — | 1 | — | — |
| | | 250 | 0.3 | 0.80 | 1:0.0012 |
| | | 250 | 0.4 | 0.90 | 1:0.0016 |
| | | 250 | 0.6 | 1.10 | 1:0.0024 |
| | | 125 | 0.4 | 0.65 | 1:0.0032 |
| | | 125 | 0.6 | 0.85 | 1:0.0048 |
| | | 125 | 0.8 | 1.05 | 1:0.0064 |
| S. aureus ATCC#6538 | 24 hrs | 200 | — | — | — |
| | | — | 6 | — | — |
| | | 100 | 5 | 1.33 | 1:0.0500 |
| | | 50 | 5 | 1.08 | 1:0.1000 |
| | | 25 | 6 | 1.13 | 1:0.2400 |
| | 48 hrs | 200 | — | — | — |
| | | — | 8 | — | — |
| | | 100 | 8 | 1.50 | 1:0.0800 |
| | | 50 | 8 | 1.25 | 1:0.1600 |
| | | 25 | 8 | 1.13 | 1:0.3200 |

Ca: component in ppm active concentration of OPP (ortho-phenylphenol)
Cb: component in ppm active concentration of Ag (Slow release delivery system 1)

The data in Table 5 demonstrate that there is an unexpected synergistic interaction between OPP and silver at ratios of 1:0.0004 to 1:0.2353.

TABLE 6

| Test Organisms | Contact Time | Ca | Cb | S.I. | Ca:Cb |
|---|---|---|---|---|---|
| A. niger ATCC #16404 | 3rd day | 75 | — | — | — |
| | | — | 3 | — | — |
| | | 35 | 0.2 | 0.53 | 1:0.0057 |
| | | 35 | 0.4 | 0.60 | 1:0.0114 |
| | | 35 | 0.6 | 0.67 | 1:0.0171 |
| | | 35 | 1 | 0.80 | 1:0.0286 |
| | | 35 | 2 | 1.13 | 1:0.0571 |
| | | 17 | 2 | 0.89 | 1:0.1176 |
| | | 17 | 3 | 1.23 | 1:0.1765 |
| | 7th day | 75 | — | — | — |
| | | — | 10 | — | — |
| | | 35 | 2 | 0.67 | 1:0.0571 |
| | | 35 | 3 | 0.77 | 1:0.0857 |
| | | 35 | 4 | 0.87 | 1:0.1143 |
| | | 35 | 6 | 1.07 | 1:0.1714 |
| | | 17 | 3 | 0.53 | 1:0.1765 |
| | | 17 | 4 | 0.63 | 1:0.2353 |
| | | 17 | 6 | 0.83 | 1:0.3529 |
| | | 17 | 8 | 1.03 | 1:0.4706 |
| C. albicans ATCC#10203 | 48 hrs | 150 | — | — | — |
| | | — | 8 | — | — |
| | | 75 | 3 | 0.88 | 1:0.0400 |
| | | 75 | 4 | 1.00 | 1:0.0533 |
| | | 35 | 5 | 0.86 | 1:0.1429 |
| | | 35 | 6 | 0.98 | 1:0.1714 |
| | | 35 | 8 | 1.23 | 1:0.2286 |
| | | 17 | 8 | 1.11 | 1:0.4706 |
| | 72 hrs | 150 | — | — | — |
| | | — | 8 | — | — |
| | | 75 | 4 | 1.00 | 1:0.0533 |
| | | 35 | 5 | 0.86 | 1:0.1429 |
| | | 35 | 6 | 0.98 | 1:0.1714 |
| | | 35 | 8 | 1.23 | 1:0.2286 |
| | | 17 | 8 | 1.11 | 1:0.4706 |
| Ps. aeruginosa ATCC#15442 | 24 hrs | 500 | — | — | — |
| | | — | 0.4 | — | — |
| | | 250 | 0.1 | 0.75 | 1:0.0004 |
| | | 250 | 0.2 | 1.00 | 1:0.0008 |
| | | 250 | 0.3 | 1.25 | 1:0.0012 |
| | | 125 | 0.3 | 1.00 | 1:0.0024 |

TABLE 6-continued

| Test Organisms | Contact Time | Ca | Cb | S.I. | Ca:Cb |
|---|---|---|---|---|---|
| | | 125 | 0.4 | 1.25 | 1:0.0032 |
| | 48 hrs | 500 | — | — | — |
| | | — | 0.6 | — | — |
| | | 250 | 0.2 | 0.83 | 1:0.0008 |
| | | 250 | 0.3 | 1.00 | 1:0.0012 |
| | | 250 | 0.4 | 1.17 | 1:0.0016 |
| | | 125 | 0.4 | 0.92 | 1:0.0032 |
| | | 125 | 0.6 | 1.25 | 1:0.0048 |
| S. aureus ATCC#6538 | 24 hrs | 200 | — | — | — |
| | | — | 6 | — | — |
| | | 100 | 5 | 1.33 | 1:0.0500 |
| | | 50 | 6 | 1.25 | 1:0.1200 |
| | | 25 | 6 | 1.13 | 1:0.2400 |
| | 48 hrs | 200 | — | — | — |
| | | — | 9 | — | — |
| | | 100 | 5 | 1.06 | 1:0.0500 |
| | | 50 | 8 | 1.14 | 1:0.1600 |
| | | 25 | 8 | 1.01 | 1:0.3200 |

Ca: component in ppm active concentration of OPP(ortho-phenylphenol)
Cb: component in ppm active concentration of Silver (Slow release delivery system 2)

The data in Table 6 demonstrate that there is an unexpected synergistic interaction between OPP and silver at ratios of 1:0.0004 to 1:0.3529.

What is claimed is:

1. A synergistic composition comprising: ortho phenylphenol and silver nitrate wherein the weight ratio of the ortho phenylphenol to the silver nitrate is between 1:0.5 and 1:0.0004.

2. The composition of claim 1 wherein the silver is obtained from a controlled release formulation.

3. A method for controlling microorganisms in an aqueous or water-containing system, the method comprising treating the system with the composition of claim 1.

4. The method of claim 3 wherein the aqueous or water-containing system is used or is present in oil or gas production, cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pools, personal care, household, industrial and institutional products, membrane and filtration systems, textiles, leather and leather production systems, or a system used therewith.

* * * * *